United States Patent [19]

Gilhousen et al.

[11] Patent Number: 5,056,109
[45] Date of Patent: Oct. 8, 1991

[54] METHOD AND APPARATUS FOR CONTROLLING TRANSMISSION POWER IN A CDMA CELLULAR MOBILE TELEPHONE SYSTEM

[75] Inventors: Klein S. Gilhousen; Roberto Padovani, both of San Diego; Charles E. Wheatley, III, Del Mar, all of Calif.

[73] Assignee: Qualcomm, Inc., San Diego, Calif.

[21] Appl. No.: 433,031

[22] Filed: Nov. 7, 1989

[51] Int. Cl.$^5$ ............... H04L 27/30; H04J 13/00; H04B 7/204

[52] U.S. Cl. .................. 375/1; 370/18; 379/59; 455/33; 455/54; 455/69

[58] Field of Search ........... 455/33, 54, 59, 69; 370/18, 50; 379/58, 59

[56] References Cited

U.S. PATENT DOCUMENTS

| | | | |
|---|---|---|---|
| 4,112,257 | 9/1978 | Frost | 379/60 |
| 4,123,718 | 10/1978 | Lampert et al. | 375/1 |
| 4,222,115 | 9/1980 | Cooper et al. | 375/1 |
| 4,225,976 | 9/1980 | Osborne et al. | 455/226 |
| 4,495,648 | 1/1985 | Giger | 445/73 |
| 4,580,262 | 4/1986 | Naylor et al. | 371/5.5 |
| 4,641,322 | 2/1987 | Hasegawa | 375/1 |
| 4,672,658 | 6/1987 | Kavehrad et al. | 379/63 |
| 4,765,753 | 8/1988 | Schmidt | 379/60 |
| 4,811,421 | 3/1989 | Havel et al. | 455/69 |

Primary Examiner—Bernarr E. Gregory
Attorney, Agent, or Firm—Russell B. Miller

[57] ABSTRACT

A power control system for a cellular mobile telephone system in which system users communicate information signals between one another via at least one cell site using code division multiple access spread spectrum communication signals. The power control system controls transmission signal power for each cellular mobile telephone in the cellular mobile telephone system wherein each cellular mobile telephone has an antenna, transmitter and receiver and each cell-site also has an antenna, transmitter and receiver. Cell-site transmitted signal power is measured as received at the mobile unit. Transmitter power is adjusted at the mobile unit in an opposite manner with respect to increases and decreases in received signal power. A power control feedback scheme may also be utilized. At the cell-site communicating with the mobile unit, the mobile unit transmitted power is measured as received at the cell-site. A command signal is generated at the cell-site and transmitted to the mobile unit for further adjusting mobile unit transmitter power corresponding to deviations in the cell site received signal power. The feedback scheme is used to further adjust the mobile unit transmitter power so as to arrive at the cell-site at a desired power level.

27 Claims, 5 Drawing Sheets

METHOD AND APPARATUS FOR CONTROLLING TRANSMISSION POWER IN A CDMA CELLULAR MOBILE TELEPHONE SYSTEM

BACKGROUND OF THE INVENTION

I. Field of the Invention

The present invention relates to cellular mobile telephone systems. More specifically, the present invention relates to a novel and improved method and apparatus for controlling transmitter power in a code division multiple access (CDMA) cellular mobile telephone system.

II. Description of the Related Art

The use of code division multiple access (CDMA) modulation techniques is one of several techniques for facilitating communications in which a large number of system users are present. Although other techniques such as time division multiple access (TDMA), frequency division multiple access (FDMA) and AM modulation schemes such as amplitude companded single sideband (ACSSB) are known, CDMA has significant advantages over these other techniques. The use of CDMA techniques in a multiple access communication system is disclosed in U.S. Pat. application Ser. No. 06/921,261, filed Oct. 17, 1986, entitled "SPREAD SPECTRUM MULTIPLE ACCESS COMMUNICATION SYSTEM USING SATELLITE OR TERRESTRIAL REPEATERS", now U.S. Pat. No. 4,901,307 assigned to the assignee of the present invention, the disclosure thereof incorporated by reference.

In the just mentioned patent, a multiple access technique is disclosed where a large number of mobile telephone system users each having a transceiver communicate through satellite repeaters or terrestrial base stations (also known as cell-sites stations, or for short cell-sites) using code division multiple access (CDMA) spread spectrum communication signals. In using CDMA communications, the frequency spectrum can be reused multiple times thus permitting an increase in system user capacity. The use of CDMA results in a much higher spectral efficiency than can be achieved using other multiple access techniques. In a CDMA system, increases in system capacity may be realized by controlling the transmitter power of each mobile user so as to reduce interference to other system users.

In the satellite application of the CDMA communication techniques, the mobile unit transceiver measures the power level of a signal received via a satellite repeater. Using this power measurement, along with knowledge of the satellite transponder downlink transmit power level and the sensitivity of the mobile unit receiver, the mobile unit transceiver can estimate the path loss of the channel between the mobile unit and the satellite. The mobile unit transceiver then determines the appropriate transmitter power to be used for signal transmissions between the mobile unit and the satellite, taking into account the path loss measurement, the transmitted data rate and the satellite receiver sensitivity.

The signals transmitted by the mobile unit to the satellite are relayed by the satellite to a Hub control system earth station. The Hub measures the received signal power from signals transmitted by each active mobile unit transceiver. The Hub then determines the deviation in the received power level from that which is necessary to maintain the desired communications. Preferably the desired power level is a minimum power level necessary to maintain quality communications so as to result in a reduction in system interference.

The Hub then transmits a power control command signal to each mobile user so as to adjust or "fine tune" the transmit power of the mobile unit. This command signal is used by the mobile unit to change the transmit power level closer to a minimum level required to maintain the desired communications. As channel conditions change, typically due to motion of the mobile unit, both the mobile unit receiver power measurement and the power control feedback from the Hub continually readjust the transmit power level so as to maintain a proper power level. The power control feedback from the Hub is generally quite slow due to round trip delays through the satellite requiring approximately ½ of a second of propagation time.

One important difference between satellite or terrestrial base stations systems are the relative distances separating the mobile units and the satellite or cell-site. Another important different in the satellite versus the terrestrial system is the type of fading that occurs in these channels. Thus, these differences require various refinements in the approach to system power control for the terrestrial system.

In the satellite/mobile unit channel, i.e. the satellite channel, the satellite repeaters are normally located in a geosynchronous earth orbit. As such, the mobile units are all at approximately the same distance from the satellite repeaters and therefore experience nearly the same propagation loss. Furthermore, the satellite channel has a propagation loss characteristic that follows approximately the inverse square law, i.e. the propagation loss is inversely proportional to the square of the distance between the mobile unit and the satellite repeater in use. Accordingly, in the satellite channel the variation in path loss due to distance variation is typically on the order of only 1–2 dB.

In contrast to the satellite channel, the terrestrial/mobile unit channel, i.e. the terrestrial channel, the distance between the mobile units and the cell sites can vary considerably. For example, one mobile unit may be located at a distance of five miles from the cell site while another mobile unit may be located only a few feet away. The variation in distance may exceed a factor of one hundred to one. The terrestrial channel experiences a propagation loss characteristic as did the satellite channel. However, in the terrestrial channel the propagation loss characteristic corresponds to an inverse fourth-power law, i.e. the path loss is proportional to the inverse of the path distance raised to the fourth power. Accordingly, path loss variations may be encountered which are on the order of over 80 dB in a cell having a radius of five miles.

The satellite channel typically experiences fading that is characterized as Rician. Accordingly the received signal consists of a direct component summed with a multiply reflected component having Rayleigh fading statistics. The power ratio between the direct and reflected component is typically on the order of 6–10 dB, depending upon the characteristics of the mobile unit antenna and the environment about the mobile unit.

Contrasting the satellite channel with the terrestrial channel, the terrestrial channel experiences signal fading that typically consists of the Rayleigh faded component without a direct component. Thus, the terrestrial channel presents a more severe fading environment than the satellite channel where Rician fading is the dominant fading characteristic.

The Rayleigh fading characteristics in the terrestrial channel signal is caused by the signal being reflected from many different features of the physical environment. As a result, a signal arrives almost simultaneously at a mobile unit receiver from many directions with different transmission delays. At the UHF frequency bands usually employed for mobile radio communications, including those of cellular mobile telephone systems, significant phase differences in signals traveling on different paths may occur. The possibility for destructive summation of the signals may result, with on occasion deep fades occurring.

Terrestrial channel fading is a very strong function of the physical position of the mobile unit. A small change in position of the mobile unit changes the physical delays of all the signal propagation paths, which further results in a different phase for each path. Thus, the motion of the mobile unit through the environment can result in a quite rapid fading process. For example, in the 850 MHz cellular radio frequency band, this fading can typically be as fast as one fade per second per mile per hour of vehicle speed. Fading on this order can be extremely disruptive to signals in the terrestrial channel resulting in poor communication quality. However, additional transmitter power can be used to overcome the problem of fading.

The terrestrial cellular mobile telephone system typically requires a full-duplex channel to be provided in order to allow both directions of the telephone conversation to be simultaneously active such as provided by the conventional wired telephone system. This full-duplex radio channel is normally provided by using one frequency band for the outbound link, i.e. transmissions from the cell-site transmitter to the mobile unit receivers. A different frequency band is utilized for the inbound link, i.e. transmissions from the mobile unit transmitters to the cell-site receivers. According, this frequency band separation allows a mobile unit transmitter and receiver to be active simultaneously without feedback or interference from the transmitter into the receiver.

The use of different frequency bands has significant implications in the power control of the cell-site and mobile unit transmitters. Use of different frequency bands causes the multipath fading to be independent processes for the inbound and outbound channels. A mobile unit cannot simply measure the outbound channel path loss and assume that the same path loss is present on the inbound channel.

It is therefore, an object of the present invention to provide a novel and improved method and apparatus for controlling in the terrestrial channel transmitter power so as to overcome deleterious fading without causing unnecessary system interference which can adversely affect overall system capacity.

SUMMARY OF THE INVENTION

In a terrestrial CDMA cellular mobile telephone system, it is desirable that the transmitter power of the mobile units be controlled so as to produce at the cell site receiver a nominal received signal power from each and every mobile unit transmitter operating within the cell. Should all of the mobile unit transmitters within an area of coverage of the cell-site have transmitter power controlled accordingly the total signal power received at the cell-site would be equal to the nominal receiver power of the mobile unit transmitted signal multiplied by the number of mobile units transmitting within the cell. To this is added the noise power received at the cell-site from mobile units in adjacent cells.

The CDMA receivers of the cell-site respectively operate by converting a wideband CDMA signal from a corresponding one of the mobile unit transmitters into a narrow band digital information carrying signal. At the same time, other received CDMA signals that are not selected remain as wide band noise signals. The bit-error-rate performance of the cell-site receiver is thus determined by the ratio of the power of the desired signal to that of the undesired signals received at the cell-site, i.e., the received signal power in the desired signal transmitted by the selected mobile unit transmitter to that of the received signal power in undesired signals transmitted by the other mobile unit transmitters. The bandwidth reduction processing, a correlation process which results in what is commonly called "processing gain", increases the signal to noise interference ratio from a negative value to a positive value thus allowing operation within an acceptable bit-error-rate.

In a terrestrial CDMA cellular mobile telephone system it is extremely desirable to maximize the capacity in terms of the number of simultaneous telephone calls that may be handled in a given system bandwidth. System capacity can be maximized if the transmitter power of each mobile unit is controlled such that the transmitted signal arrives at the cell-site receiver at the minimal signal to noise interference ratio which allows acceptable data recovery. If a signal transmitted by a mobile unit arrives at the cell-site receiver at a power level that is too low, the bit-error-rate may be too high to permit high quality communications. On the other hand if the mobile unit transmitted signal is at a power level that is too high when received at the cell site receiver, communication with this particular mobile unit will be acceptable. However, this high power signal acts as interference to other mobile unit transmitted signals that are sharing the same channel, i.e. bandwidth. This interference may adversely affect communications with other mobile units unless the total number of communicating mobile units is reduced.

The path loss of signals in the UHF frequency band of the cellular mobile telephone channel can be characterized by two separate phenomena, average path loss and fading. The average path loss can be described statistically by a log-normal distribution whose mean is proportional to the inverse fourth-power of the path distance, and whose standard deviation is approximately equal to 8 dB. The second phenomena is a fading process caused by multipath propagation of the signals which is characterized by a Rayleigh distribution. The average path loss, which is a log-normal distribution, can be considered to be the same for both the inbound and outbound frequency bands, as is for the conventional cellular mobile telephone systems. However, as mentioned previously Rayleigh fading is an independent phenomena for the inbound and outbound link frequency bands. The log-normal distribution of the average path loss is a relatively slow varying function of position. In contrast, the Rayleigh distribution varies relatively fast as a function of position.

In the present invention, a CDMA approach to multiple user access in a cellular mobile telephone system is implemented. In such a system all the cell-sites in a region transmit, a "pilot" signal of the same frequency and code. The use of a pilot signal in CDMA systems is well known. In this particular application, the pilot signal is used by the mobile units for initial synchronization of the mobile unit receiver. The pilot signal is also used as a phase and frequency reference and a time reference for demodulation of the digital speech signals transmitted by the cell-site.

In the present invention, each mobile unit estimates the path loss in signals transmitted from the cell-site to the mobile unit. In order to make this signal path loss estimate, the power level of the cell-site transmitted signals, as received at the mobile unit, are measured. The mobile unit thus measures the pilot signal power as received from the cell-site to which the mobile unit is communicating. The mobile unit also measures the power level sum of all cell-site transmitted signals as received at the mobile unit. The power level sum measurement as described in further detail later herein, is necessary to handle cases in which the mobile unit might temporarily obtain a better path to a more distant cell-site than to a normally preferred closest cell-site.

The outbound link path loss estimate is filtered using a non-linear filter. The purpose of the non-linearity in the estimation process is to permit a rapid response to a sudden improvement in the channel while only allowing a much slower response to a sudden degradation in the channel. The mobile unit in response to a sudden improvement in the channel thus suddenly reduces mobile unit transmitter transmit power.

Should the channel for one mobile unit suddenly improve, then the signal as received at the cell-site from this mobile unit will suddenly increase in power. This sudden increase in power causes additional interference to all signals sharing the same wide band channel. A rapid response to the sudden improvement will thus reduce system interference.

A typical example of a sudden improvement in the channel occurs when a mobile unit is moving through an area that is shadowed by a large building or other obstruction and then drives out of the shadow. The channel improvement, as a result of the vehicle movement, can take place on the order of a few tens of milliseconds. As the mobile unit drives out of the shadow, the outbound link signal as received by the mobile unit will suddenly increase in strength.

The outbound link path loss estimate at the mobile unit is used by the mobile unit to adjust the mobile unit transmitter power. Thus, the stronger the received signal, the lower the mobile unit transmitter power will be. Reception of a strong signal from the cell-site indicates that the mobile unit is either close to the cell-site or else an unusually good path to the cell-site exists. Reception of a strong signal means that a relatively smaller mobile unit transmitter power level is required in order to produce a nominal received power at the cell-site in transmissions by the mobile unit.

In the case where there is a temporary but yet sudden degradation in the channel it is desirable that a much slower increase in mobile unit transmitter power be permitted. This slow increase in mobile unit transmitter power is desired so as to prohibit an unnecessarily rapid increase in mobile unit transmit power which increases the interference to all other mobile units. Thus a temporary degradation in one mobile unit channel will be tolerated in order to prevent a degradation of all mobile unit channels.

In the case of a sudden degradation in the channel, the non-linear filter prevents the mobile transmitter power from being increased at a high rate in response to the sudden decrease in signal power in signals received at the mobile unit. The rate of increase of the mobile unit transmitter transmit power must generally be limited to the rate of a closed loop power adjustment command transmitted from the cell-site, as described below, can reduce the mobile unit transmitter transmit power. Using the cell-site generated power adjustment commands, the mobile unit transmitter power will be prevented from being increased to a level significantly higher than the level required for communications, particularly when a sudden channel degradation occurs in only the outbound link path and not in the inbound link path.

It should be noted that it is undesirable to simply use a slow response on the mobile unit transmitter power control in an attempt to separate the fast Rayleigh fading from the slow fading due to distance and terrain. A slow response in the mobile unit transmitter power control is undesirable because the possibility of sudden improvements and fades that affect the inbound and outbound channels equally. If the response to a sudden improvement were to be slowed down by a filter, then there would be frequent occasions when the mobile unit transmitter power would be quite excessive and cause interference to all other mobile users. Thus the present invention uses a two time constant, non-linear approach in estimating the path loss.

In addition to measuring the received signal strength in the mobile unit, it is also desirable for the processor in the mobile unit to know the cell-site transmitter power and antenna gain (EIRP), the cell-site G/T (receive antenna gain G divided by receiver noise level T), the mobile unit antenna gain, and the number of calls active at this cell-site. This information allows the mobile unit processor to properly compute the reference power level for the local power setting function. This computation is done by calculating the cell-site to mobile link power budget, solving for the path loss. This path loss estimate is then used in the mobile cell-site link budget equation, solving for the mobile unit transmit power required to produce a desired signal level. This capability allows the system to have cell-sites with differing EIRP levels to correspond to the size of the cells. For example, a small radius cell need not transmit with as high a power level as a large radius cell. However, when the mobile unit is a certain distance from a low power cell, it would receive a weaker signal than from a high power cell. The mobile unit would respond with a higher transmit power than would be necessary for the short range. Hence, the desirability of having each cell-site transmit information as to its characteristics for power control.

The cell-site transmits information such as cell-site EIRP, G/T and number of active calls on a cell-site setup channel. The mobile unit receives this information when first obtaining system synchronization and continues to monitor this channel when idle for pages for calls originated within the public telephone switching network intended for the mobile unit. The mobile unit antenna gain is stored in a memory in the mobile unit at the time the mobile unit is installed in the vehicle.

As mentioned previously, mobile unit transmitter power is also controlled by a signal from the cell-site. Each cell-site receiver measures the strength of the signal, as received at the cell-site, from each mobile unit to which the cell-site is in communication with. The measured signal strength is compared to a desired signal strength level for that particular mobile unit. A power adjustment command is generated and sent to the mobile unit in the outbound link data, or voice channel, addressed to that mobile unit. In response to the cell-site power adjustment command, the mobile unit increases or decreases the mobile unit transmitter power by a predetermined amount, nominally 1 dB.

The power adjustment command is transmitted by the cell-site transmitter at a relatively high rate, typically on the order of about one command every millisecond. The rate of transmission of the power adjustment command must be high enough to permit Rayleigh fading on the inbound link path to be tracked. It is further desirable for the outbound link path Rayleigh fading impressed on the inbound link path signal to be tracked. One command per millisecond is adequate to track the fading processes for vehicle speeds in the range of 25–50 miles per hour for 850 MHz band mobile communications. It is important that the latency in determining the power adjustment command and the transmission thereof be minimized so that channel conditions will not change significantly before the mobile unit receives and responds to the signal.

To account for the independence of the two Rayleigh fading paths, the mobile unit transmitter power is also controlled by the power adjustment command from the cell-site. Each cell-site receiver measures the received signal strength from each mobile unit. The measured signal strength is compared to the desired signal strength for that mobile unit and a power adjustment command is generated. The power adjustment command is sent to the mobile unit in the outbound data or voice channel addressed to that mobile unit. This power adjustment command is combined with the mobile unit one way estimate to obtain the final value of the mobile unit transmitter power.

The power adjustment command signal is transmitted, in an exemplary embodiment, by overwriting one or more user data bits every millisecond. The modulation system employed in CDMA systems is capable of providing error detection and correction coding for user data bits. The overwrite by the power adjustment command is treated as a channel bit error or erasure and corrected by the error correction as decoded in the mobile unit receiver. Error correction coding on the power adjustment command bits in many cases may not be desirable because of the resulting increased latency in reception and response to the power command. It is also envisioned that time division multiplexing for transmission of the power adjustment command bits may be used without overwriting user data channel symbols.

The cell-site controller or processor can be used to determine the desired signal strength, as received at the cell-site, for signals transmitted by each mobile unit. The desired signal strength level values are provided to each of the cell-site receivers. The desired signal strength value is used for comparing with a measured signal strength value for generating the power adjustment command.

A system controller is utilized to command each cell-site processor as to the value of desired signal strength to use. The nominal power level can be adjusted up or down to accommodate variations in the average conditions of the cell. For example, a cell-site positioned in an unusually noisy location or geographic region might be allowed to use a higher than normal inbound power level. However, such a higher power level for in-cell operation will result in higher levels of interference to immediate neighbors of this cell. This interference can be compensated for by allowing the neighbor cells a small increase in inbound link power. Such an increase in inbound power in neighboring cells would be smaller than that of the increase given to the mobile users communicating in the high noise environment cell. It is further understood that the cell-site processor may monitor the average bit-error-rate. This data may be used by the system controller to command the cell-site processor to set an appropriate inbound link power level to assure acceptable quality communications.

It is also desirable to provide a means for controlling the relative power used in each data signal transmitted by the cell-site in response to control information transmitted by each mobile unit. The primary reason for providing such control is to accommodate the fact that in certain locations, the outbound channel link from the cell-site to the mobile unit may be unusually disadvantaged. Unless the power being transmitted to this mobile is increased, the quality may become unacceptable. An example of such a location is a point where the path loss to one or two neighboring cells is nearly the same as the path loss to the cell-site communicating with the mobile unit. In such a location, the total interference would be increased by three times over the interference seen by the mobile unit at a point relatively close to its cell-site. In addition, the interference coming from these neighboring cell-sites will not fade in unison with the desired signal as would be the case for interference coming from the desired cell-site. This situation may required 3–4 dB additional signal power to achieve adequate performance.

In another situation, the mobile unit may be located where several strong multi-path signals arrive, resulting in larger than normal interference. In such a situation, increasing the power of the desired signal relative to the interference may allow acceptable performance. At other times, the mobile unit may be located where the signal-to-interference ratio is unusually good. In such a case, the cell-site could transmit the desired signal using a lower than normal transmitter power, reducing interference to other signals being transmitted by the system.

To achieve the above objectives, the preferred embodiment includes a signal-to-interference measurement capability within the mobile unit receiver. This measurement is performed by comparing the power of the desired signal to the total interference and noise power. If the measured ratio is less than a predetermined value the mobile transmits a request to the cell-site for additional power in cell-site transmissions. If the ratio exceeds the predetermined value, the mobile unit transmits a request for a reduction in power.

The cell-site receives the power adjustment requests from each mobile and responds by adjusting the power allocated to the corresponding cell-site transmitted signal by a predetermined amount. The adjustment would usually be small, on the order of 0.5 dB, or 12%. The rate of change of power may be somewhat slower than that used for the inbound link from the mobile unit to cell-site, perhaps once per vocoder frame, or nominally once per 15 milliseconds. The dynamic range of the adjustment would also be limited to 4 dB less than nominal to about 6 dB greater than nominal.

The cell-site must also consider the power demands being made on it by all the mobiles in deciding whether to comply with the requests of any particular mobile. For example, if the cell-site is loaded to capacity, requests for additional power might be granted but only by 6% or less instead of the normal 12%. In this regime, a request for a reduction in power would still be granted at the normal 12% change.

BRIEF DESCRIPTION OF THE DRAWINGS

The features and advantages of the present invention will become more apparent from the detailed description set forth below when taken in conjunction with the drawings in which like reference characters correspond throughout and wherein.

DETAILED DESCRIPTION OF THE PREFERRED EMBODIMENTS

Figure 1:
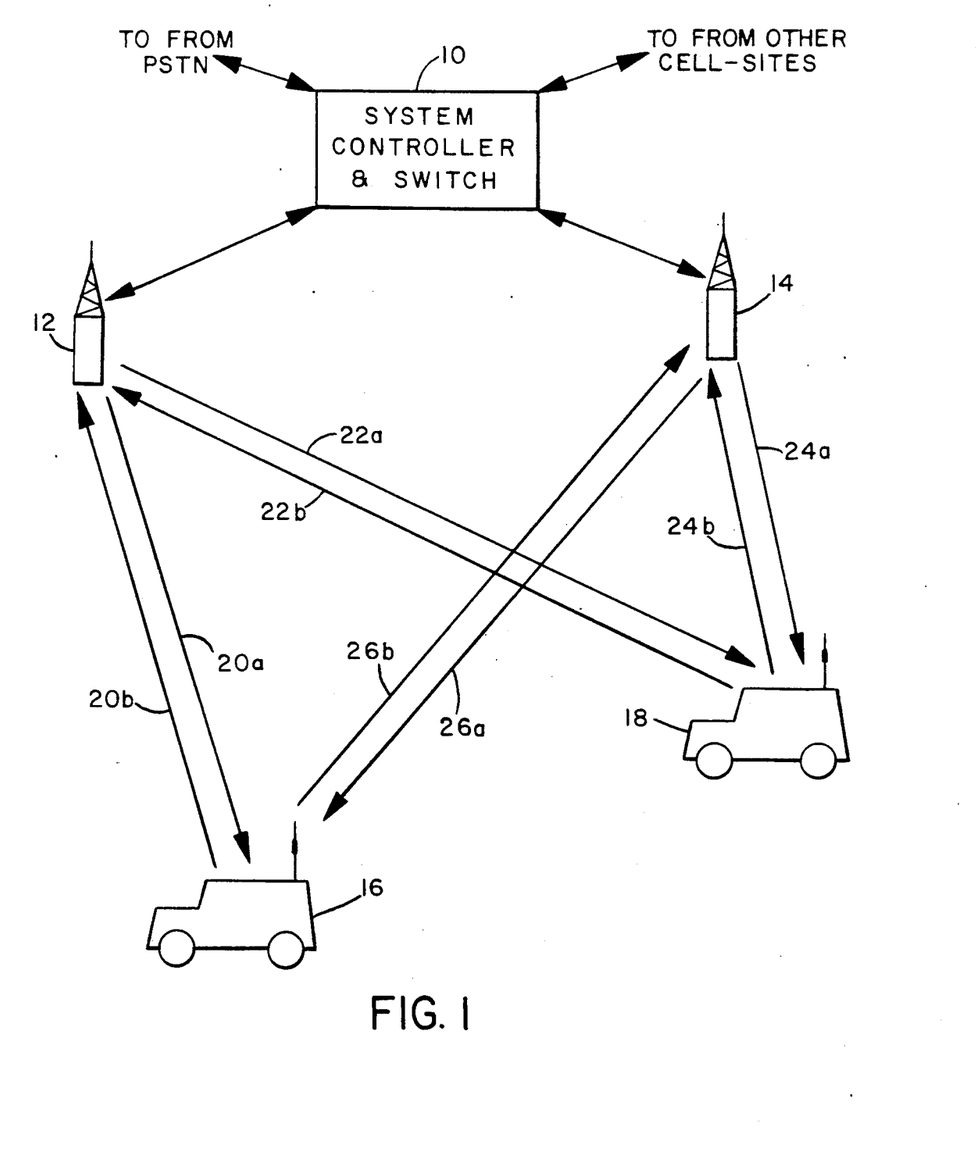
FIG. 1 is a schematic overview of an exemplary mobile cellular telephone system.

An exemplary terrestrial cellular mobile telephone system in which the present invention is embodied is illustrated in FIG. 1. The system illustrated in FIG. 1 utilizes CDMA modulation techniques in communications between the system mobile user, and the cell-sites. Cellular systems in large cities may have hundreds of cell-site stations serving hundreds of thousands of mobile telephones. The use of CDMA techniques readily facilitates increases in user capacity in systems of this size as compared to conventional FM modulation cellular systems.

In FIG. 1, system controller and switch 10, typically includes appropriate interface and processing hardware for providing system control information to the cell-sites. Controller 10 controls the routing of telephone calls from the public switched telephone network (PSTN) to the appropriate cell-site for transmission to the appropriate mobile unit. Controller 10 also controls the routing of calls from the mobile units via at least one cell-site to the PSTN. Controller 10 may direct calls between mobile users via the appropriate cell-site stations since such mobile units do not typically communicate directly with one another.

Controller 10 may be coupled to the cell-sites by various means such as dedicated telephone lines, optical fiber links or by radio frequency communications. In FIG. 1, two exemplary cell-sites, 12 and 14, along with two exemplary mobile units 16 and 18 which include cellular telephones are illustrated. Arrows 20a-20b and 22a-22b respectively define the possible communication links between cell-site 12 and mobile units 16 and 18. Similarly, arrows 24a-24b and arrows 26a-26b respectively define the possible communication links between cell-site 14 and mobile units 18 and 16. Cell-sites 12 and 14 normally transmit using equal power.

Mobile unit 16 measures the total received power in signals transmitted by cell-sites 12 and 14 upon path 20a and 26a. Similarly, mobile unit 18 measures the total received power in signals as transmitted by cell-sites 12 and 14 upon paths 22a and 24a. In each of mobile units 16 and 18, signals power is measured in the receiver where the signals are wide band signals. Accordingly, this power measurement is made prior to correlation of the received signals with a pseudonoise (PN) spectrum spreading signal.

When mobile unit 16 is closer to cell-site 12, the received signals power will be dominated by the signal traveling path 20a. When mobile unit 16 is nearer to cell-site 14, the received power will be dominated by the signals traveling on path 26a. Similarly, when mobile unit 18 is closer to cell-site 14, the received power will be dominated by the signals on path 24a. When mobile unit 18 is closer to cell-site 12, the received power will be dominated by the signals traveling on path 22a.

Each of mobile units 16 and 18 uses the resultant measurement, together with knowledge of the cell-site transmitter power and the mobile unit antenna gain to estimate the path loss to the closest cell-site. The estimated path loss, together with knowledge of the mobile antenna gain and the cell-site G/T is used to determine the nominal transmitter power required to obtain the desired carrier-to-noise ratio in the cell-site receiver. The knowledge by the mobile units of the cell-site parameters may be either fixed in memory or transmitted in cell-site information broadcast signals, setup channel, to indicate other than nominal conditions for a particular cell-site.

As a result of the determination of the mobile unit nominal transmit power, in the absence of Rayleigh fading and assuming perfect measurements, the mobile unit transmitted signals will arrive at the nearest cell-site precisely at the desired carrier-to-noise ratio. Thus the desired performance will be obtained with the minimum amount of mobile unit transmitter power. The minimization of the mobile unit transmitted power is important in a CDMA system because each mobile unit causes interference to every other mobile unit in the system. In minimizing the mobile unit transmitter power, system interference will be held to a minimum, thus allowing additional mobile users to share the frequency band. Accordingly, system capacity and spectral efficiency is maximized.

Figure 2A:
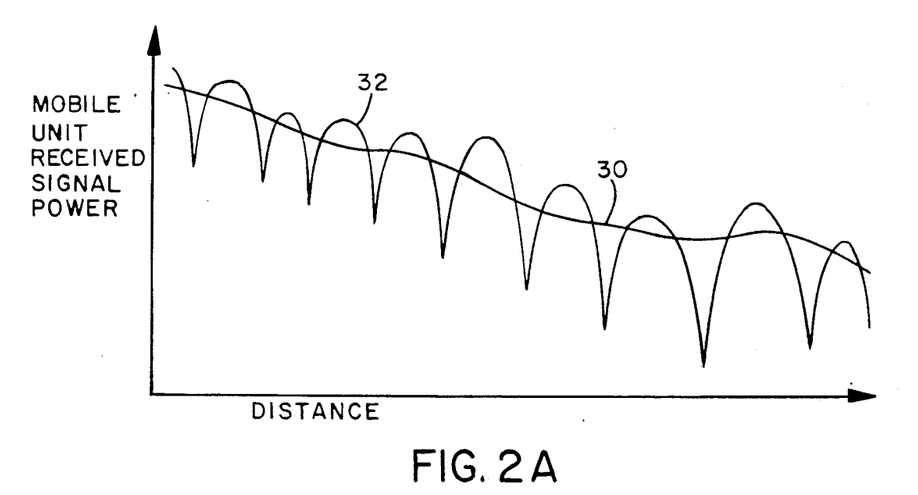
FIGS. 2A-2D illustrate, in a series of graphs, mobile unit received signal strength and transmit power as a function of distance.

FIG. 2A illustrates the effect of both Rayleigh fading as a function of distance on the strength of the cell-site transmitted signal as received at a mobile unit. The average path loss, indicated by curve 30, is determined primarily by the fourth-power of the distance between the cell-site and the mobile unit, and by the shape of the terrain between them. As distance increases between the mobile unit and the cell-site, signal power decreases as received at the mobile unit for a constant power transmitted cell-site signal. The average path loss is the same for both directions of the link, and typically exhibits a log-normal distribution about the average path loss.

In addition to the slowly varying log-normal average path loss, the rapid fading up and down around the average path loss is caused by the existence of multiple path signal propagation. The signals arrive from these multiple paths in random phase and amplitude, resulting in the characteristic Rayleigh fading. Curve 32, as illustrated in FIG. 2A, represents the variation in signal path loss as a result of Rayleigh fading. The Rayleigh fading is typically independent for the two directions of the cell-site/mobile unit communication link, i.e. outbound and inbound channels. For example, when the outbound channel is fading, the inbound channel is not necessarily fading at the same time.

Figure 2B:
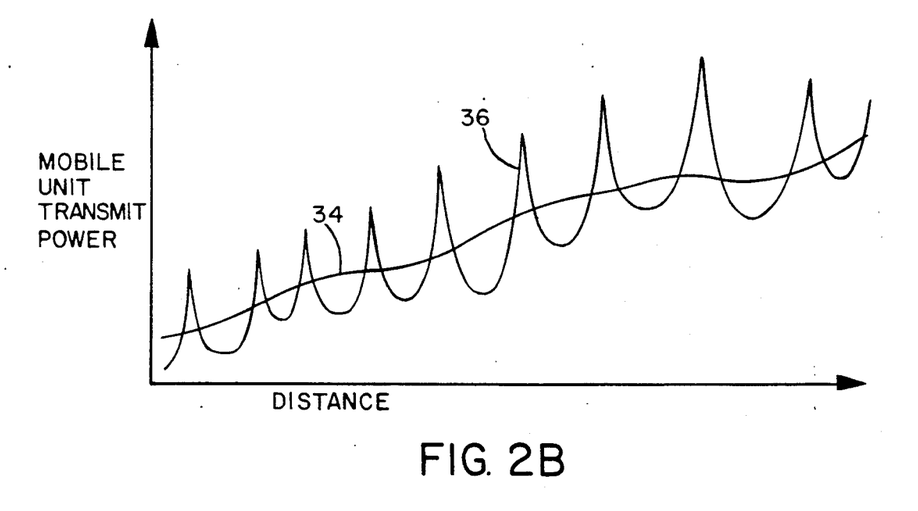

FIG. 2B illustrates the mobile unit transmitter power adjusted to correspond to the link path signal strength of FIG. 2A. In FIG. 2B, curve 34 represents the desired average transmit power corresponding to the average path loss of curve 30 of FIG. 2A. Similarly, curve 36 corresponds to the mobile unit transmitter power responding to the Rayleigh fading as represented by curve 32 of FIG. 2A. As the Rayleigh faded signal, curve 32 of FIG. 2A, decreases in signal strength, rapid increases in transmitter power result. These rapid upward excursions of transmitter power can result in deleterious effects in overall system performance. Therefore, the present invention envisions the use of a non-linear filter to control rapid upward excursions, or increases, in transmitter power. Furthermore, the present invention also utilizes closed loop power adjustment feedback from the cell-site to adjust mobile unit transmitter power.

Figure 2C:
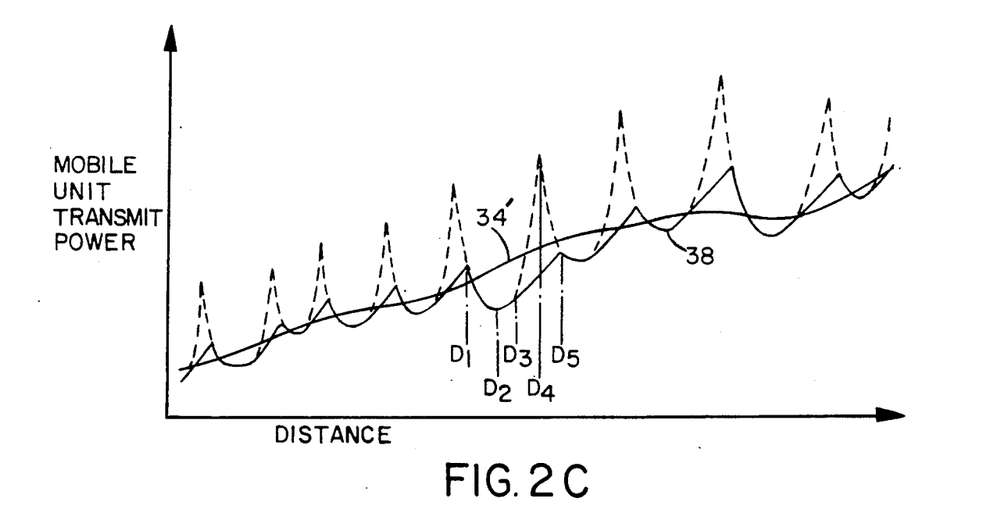

FIG. 2C illustrates the mobile unit transmitter power corresponding to FIG. 2A without taking into consideration the cell-site closed loop power adjustment feedback. In FIG. 2C the desired average transmit power, as represented by curve 34', corresponds to the mobile unit received signal strength of curve 30 of FIG. 2A. Curve 38 illustrates the transmitter power utilizing the non-linear filter in power control of the present invention. The rapid upward excursions in transmitter power, as indicated by the dashed lines of FIG. 2C and correspond to the upward excursions in curve 36 of FIG. 2B, are significantly reduced. In curve 38, the upward excursions are significantly reduced by setting the rate of increase in transmit power to a fixed value. The resulting variation in transmitter power relative to the desired transmit power is both limited in dynamic range and in rate of change. This limitation allows the closed loop power adjustment feedback process to be easier to implement and to be more effective at a much lower control data rate. Transmit power, as indicated by curve 38, is permitted to decrease at a much greater rate than an increase.

As distance increases from the points marked $D_1$–$D_2$, transmitter power decreases rather quickly corresponding to a sudden improvement in the channel. Between the distance points marked $D_2$–$D_3$ the channel degrades with a corresponding increase in transmitter power. The change in degradation is not so significant such that the non-linear filter maximum rate limits the rate of increase in transmitter power.

As distance increases as from the distance points marked $D_3$–$D_4$, the channel degrades much more rapidly than the non-linear filter will permit an increase in transmitter power. During this period, transmitter power increases at the maximum rate permitted by the non-linear filter. During the distance change indicated by marks $D_4$–$D_5$, the channel begins improving. However, as the quality of the channel improves the transmitter power continues to increase at the maximum rate until transmitter power is sufficient to meet the desired level such as at mark $D_5$.

It is desirable to eliminate the upward excursions in transmitter power which may cause unnecessary system interference. Should a better path to another cell-site occur, which would result in unnecessary interference in the system, quality communications in the system may be maintained by limiting the rate of increase in transmitter power.

Figure 2D:
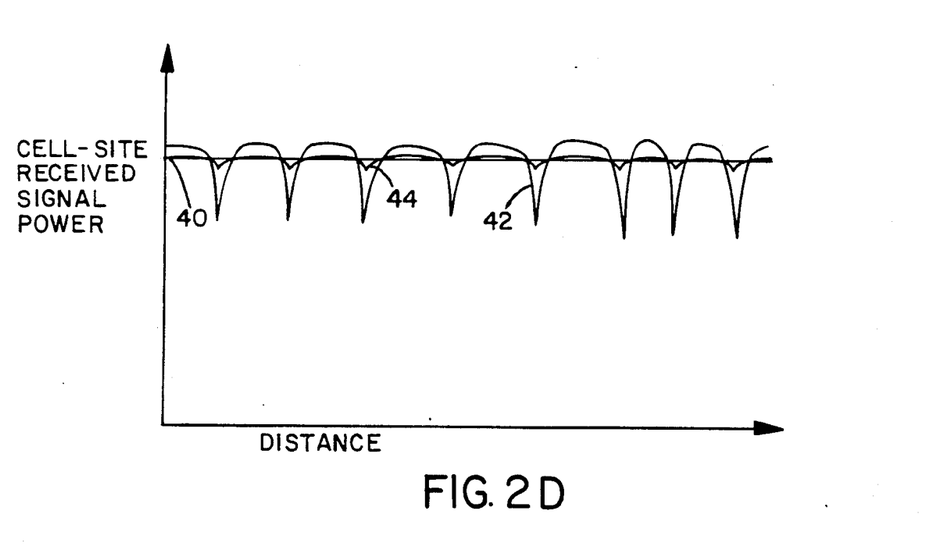

FIG. 2D is a graph illustrating the cell-site received signal power strength with respect to transmissions of the mobile unit as it travels from the cell-site. Curve 40 indicates the desired average received signal power at the cell-site for a signal transmitted from a mobile unit. It is desirable that the average received signal power be at a constant level, yet a minimum necessary to assure a quality communication link with the mobile unit. Corrections are made at the mobile unit to correct for Rayleigh fading in the cell-site transmitted signal.

The mobile unit transmitted signal experiences Rayleigh fading before arriving at the cell-site receiver. The signal received at the cell-site is therefore a signal of constant average received power level but still with the Rayleigh fading of the inbound channel impressed thereupon. Curve 42 represents the Rayleigh fading that occurs on the inbound signal.

Additionally, there is the possibility that the mobile unit may come to rest at a place where the outbound link is not faded but yet the inbound link is severely faded. Such a condition would disrupt communications unless an additional mechanism is employed to compensate for the inbound channel Rayleigh fading. Such a mechanism is the closed loop power adjustment command process employed at the cell-site for adjusting the mobile unit transmitter power. Such a power adjustment compensates for the Rayleigh fading on the inbound channel. In FIG. 2D, curve 44 illustrates the mobile unit transmitted signal power as received at the cell-site when compensating for average path loss and Rayleigh fading on both the inbound and outbound channels. As can be seen in FIG. 2D curve 44 follows close to curve 40 except for instances of severe fading where the fading process is minimized by the closed loop control.

Figure 3:
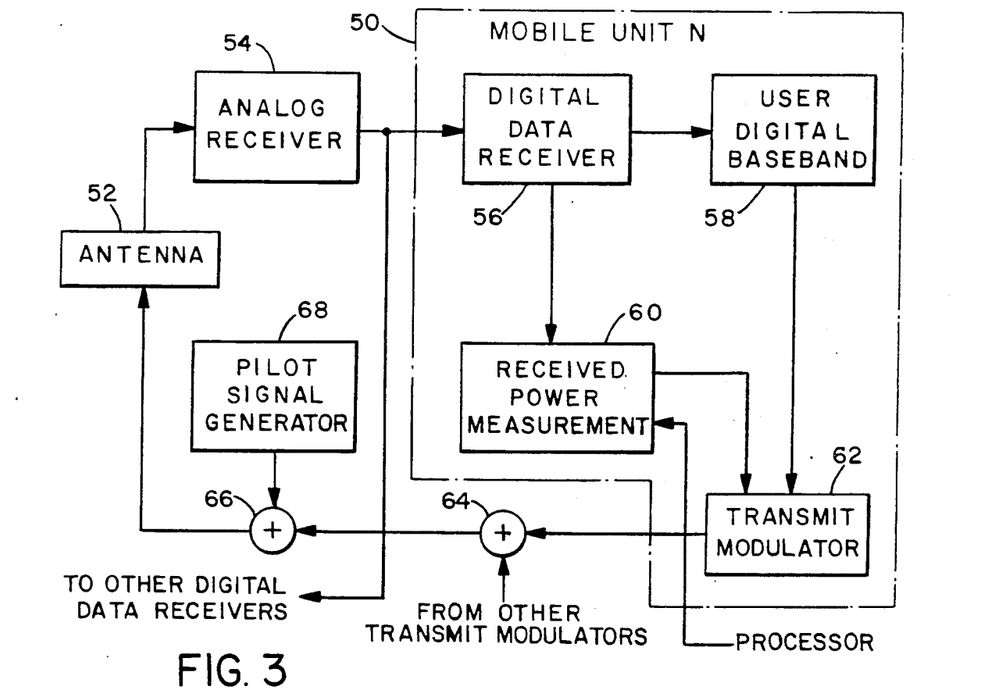
FIG. 3 is a block diagram of a cell-site with particular reference to the power control features of the present invention.

In FIG. 3 antenna 52 is provided for receiving multiple mobile unit transmitted signals which are then provided to analog receiver 54 for amplification, frequency downconversion and IF processing of the received RF signal. The analog signals output from receiver 54 are provided to a plurality of receiver modules for extraction of user directed information signals, generation of power adjustment commands, and modulation of user input information signals for transmission. One such module used in communications with a particular mobile unit, such as mobile unit N, is module 50. Thus the output of receiver 54 is provided to a plurality of these modules including module 50.

Module 50 comprises digital data receiver 56, user digital baseband circuit 58, received power measurement circuitry 60 and transmit modulator 62. Digital data receiver 56 receives the wideband spread spectrum signals for correlating and despreading the mobile unit N transmitted signal to a narrow band signal for transfer to an intended recipient communicating with mobile unit N. Digital data receiver 56 provides the narrow band digital signals to user digital baseband circuitry 58. Digital data receiver 56 also provides the narrow band signal to received power measurement circuitry 60.

Received power measurement circuitry 60 measures the power level in the received signal from mobile unit N. Received power measurement circuitry 60 in response to the measured level of power generates a power adjustment command which is input to transmit modulator 62 for transmission to mobile unit N. As previously discussed, the data bits in the power adjustment command are used by mobile unit N in adjusting mobile unit transmitter power.

When the received power measurement is greater than the preset level provided by a cell-site processor (not shown), an appropriate power adjustment command is generated. Should the received power measurement be less than the preset level, the power adjustment command data bits are generated and indicate that an increase in mobile unit transmitter power is necessary. Similarly, if the received measurement is greater than the preset level, the power adjustment command is generated such that the mobile unit transmitter power is reduced. The power adjustment command is utilized to maintain a nominal received power level at the cell-site.

The signal output from digital data receiver 56 is provided to user digital baseband circuitry 58 where it is interfaced for coupling to the intended recipient via the system controller and switch. Similarly, baseband circuitry 58 receives user information signals intended for mobile unit N and provides them to transmit modulator 62.

Transmit modulator 62 spread spectrum modulates the user addressable information signals for transmission to mobile unit N. Transmit modulator 62 also receives the power adjustment command data bits from received power measurement circuitry 60. The power adjustment command data bits are also spread spectrum modulated for transmission to mobile unit N. Transmit modulator 62 provides the spread spectrum modulated signal to summer 64 where it is combined with spread spectrum signals from other module transmit modulators also located at the cell-site.

The combined spread spectrum signals are input to summer 66 where they are combined with a pilot signal provided by pilot signal generator 68. These combined signals are then provided to circuitry (not shown) for frequency upconversion from the IF frequency band to the RF frequency band and amplified. The RF signals are then provided to antenna 52 for transmission. Although not illustrated transmit power control circuitry may be disposed between summer 66 and antenna 52. This circuitry, under control of the cell-site processor, is responsive to power adjustment command signals transmitted by the mobile unit, demodulated at the cell-site receiver and provided to the cell-site control processor for coupling to the circuitry.

Figure 4:
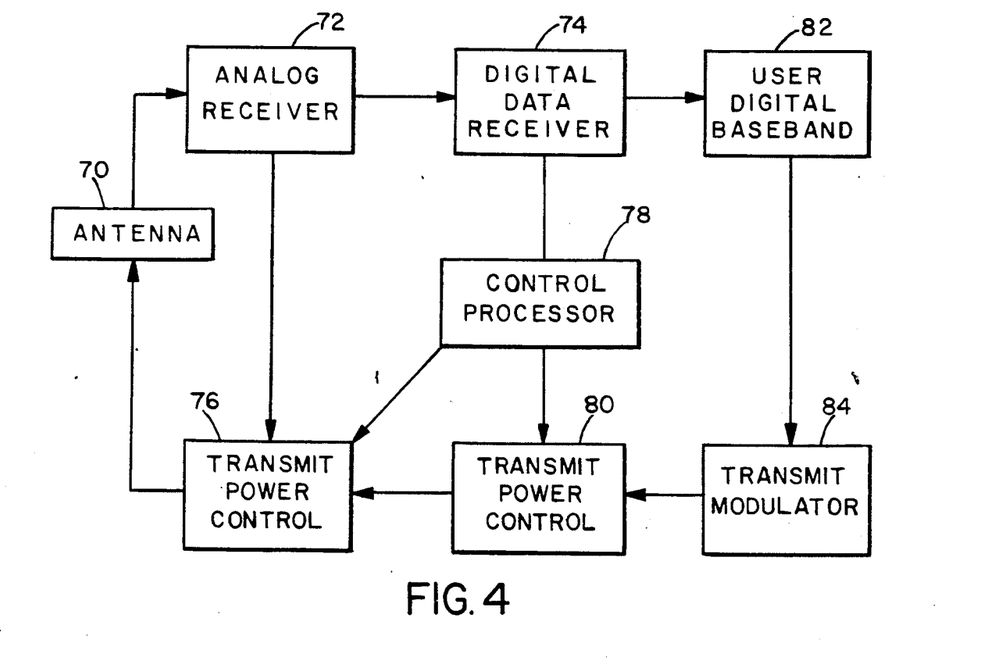
FIG. 4 is a block diagram of the mobile unit with particular reference to the power control features of the present invention.

In FIG. 4, the mobile unit, such as mobile unit N, includes an antenna 70 for collecting cell site transmitted signals and radiating mobile unit generated CDMA signals. Mobile unit N receives the pilot signal, setup channel signals and the mobile unit N addressed signals using antenna 70, analog receiver 72 and digital data receiver 74. Receiver 72 amplifies and frequency downconverts the received RF CDMA signals to IF, and filters the IF signals. The IF signals are output to digital data receiver 74 for digital processing. Receiver 72 also includes circuitry for performing an analog measurement of the combined power of the received signals. This power measurement is used to generate a feedback signal that is provided to transmit power control circuitry 76 for controlling transmit power.

Digital data receiver 74 is used for despreading and correlating the received signals addressed to mobile unit N. Receiver 74 also separates the digital data from the power adjustment command generated by the cell site. The power adjustment command data bits are sent to control processor 78. Processor 78 generates a transmit power control command that is provided to transmit power control circuitry 80. Processor 78 also provides a level set command to transmit power control circuitry 76. Further details on the interaction of receiver 72, transmit power control 76 and 80, and processor are described in further detail with reference to FIG. 5.

Receiver 74 also provides data such as digitized encoded speech to user digital baseband circuitry 82 for decoding and interface with the user. Baseband circuitry 82 includes interface hardware for coupling receiver 74 and transmit modulator 82 to the user handset (not shown).

Data to be transmitted is provided through baseband circuitry 82 where it is encoded and provided to transmit modulator 84. The data is spread spectrum modulated by transmit modulator 84 according to an assigned spreading code. The spread spectrum signals are output from transmit modulator 84 to transmit power control circuitry 80. The signal power is adjusted in accordance with the transmit power control command provided by control processor 78. This power adjusted signal is provided from transmit power control circuitry 80 to transmit power control circuitry 76 where the signal is adjusted in accordance with the analog measurement control signal. Although illustrated as two separate units for controlling the transmit power, the power level could be adjusted by a single variable gain amplifier with two input control signals combined before being applied to the variable gain amplifier. However in the illustrated exemplary embodiment the two control functions are shown as separate elements.

In the operation of the power control circuitry illustrated in FIG. 4, receiver 72 measures the combined power level of all signals received from all cell-sites. These power level measurement results are used in controlling the power level as set by transmit power control circuitry 76. Transmit power control circuitry 76 includes circuitry in which the rate of increase transmitter power is limited by a non-linear filter as previously discussed. The rate of increase is set to be no faster than the rate at which transmit power control circuitry 80 can turn the power down in response to a series of downward commands from the cell-site and processed by receiver 74 and processor 78.

Figure 5:
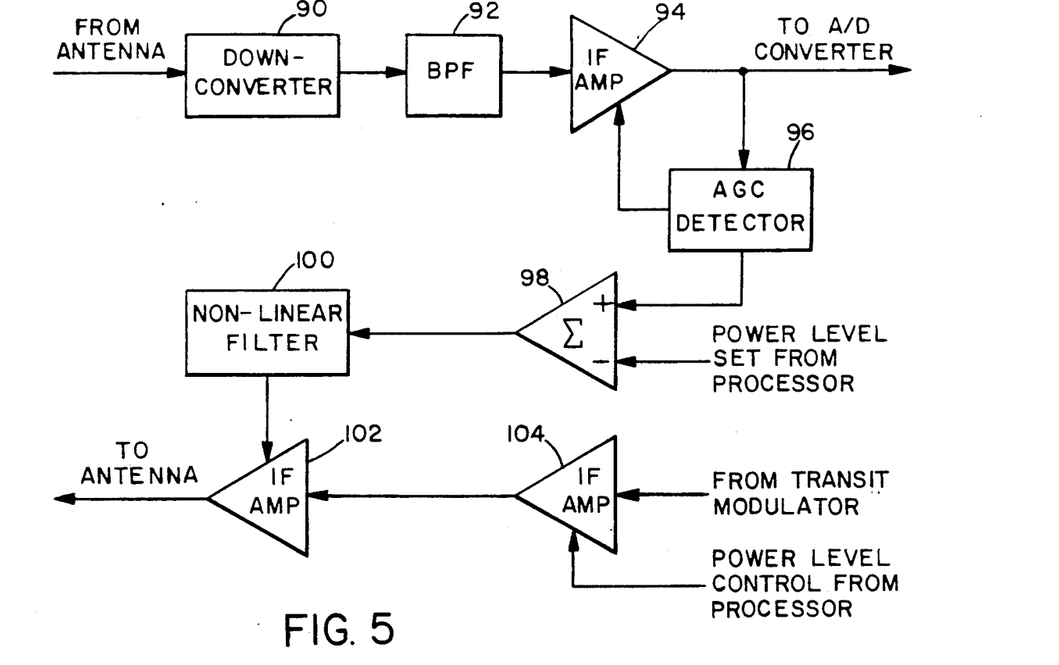
FIG. 5 is a block diagram illustrating in further detail the power control features of the mobile unit of FIG. 4.

FIG. 5 illustrates in further detail the power control aspect of mobile unit N discussed with reference to FIG. 4. In FIG. 5, received RF signals from the antenna are provided to frequency downconverter 90 where the received RF signals are converted to an IF frequency. The IF frequency signals are coupled to bandpass filter 92 where out of band frequency components are removed from the signals.

The filtered signals are output from filter 92 to variable gain IF amplifier 94 where the signals are amplified. The amplified signals are output from amplifier 94 to an analog to digital (A/D) converter (not shown) for digital signal processing operations on the signals. The output of amplifier 94 is also coupled to automatic gain control (AGC) detector circuit 96.

AGC detector circuit 96 generates a gain control signal which is coupled to a gain control input of amplifier 94. This gain control signal is used to control the gain of the amplifier 94 so as to maintain a constant average power level as output from amplifier 94 to the A/D converter.

AGC detector circuit 96 also provides an output to one input of comparator 98. The other input of comparator 98 is provided with a level set signal from the mobile unit processor (not shown). This level set signal is indicative of a desired transmitter reference power level. These input signals are compared by comparator 98 with the comparison signal provided to a non-linear filter circuit 100. This comparison signal corresponds to a deviation in the received power measurement from a desired mobile unit transmitter power level.

Filter 100 may be configured as a simple resistor-diode-capacitor circuit. For example, the input to the circuit is a common node shared two resistors. The other end of each resistor is coupled to a respective diode. The diodes are reversed in their connection to the resistors and the other end of each diode coupled together as a common node as an output of the filter. A capacitor is coupled between the diode common node and ground. The filter circuit is designed to limit the rate of power increase to less than 1 dB per millisecond. The rate of power decrease is typically set to be about ten times faster than the rate of power increase, i.e. 10 dB per millisecond. The output of filter 100 is provided as a power level control signal input to the gain control input of variable gain IF amplifier 102.

AGC detector circuit 96, comparator 98 and filter 100 estimate received mobile unit signal power and the power correction necessary for the mobile unit transmitter. This correction is used to maintain a desired transmitter power level in conditions of fading on the outbound channel that are common to the inbound channel.

Transmit modulator circuit 84 of FIG. 4, provides a low power, IF frequency spread spectrum signal to an input of variable gain IF amplifier 104. Amplifier 104 is gain controlled by a power level control signal from processor 78 (FIG. 4). This power level control signal is derived from the closed loop power adjustment command signal transmitted by the cell-site and processed by the mobile unit as discussed with reference to FIG. 4.

The power adjustment command signal consists of a sequence of power-up and power-down commands that are accumulated in the mobile unit processor. The mobile unit control processor starts with the gain control level set to a nominal value. Each power-up command increases the value of a gain control command corresponding to a resultant approximate 1 dB increase in amplifier gain. Each power-down command decreases the value of the gain control command, corresponding to a resultant approximate 1 dB decrease in amplifier gain. The gain control command is converted to analog form by a digital to analog (D/A) converter (not shown) before applied to amplifier 104 as the power level control signal.

The mobile unit reference power level may be stored in the memory of the control processor. In the alternative the mobile unit reference power level may be contained within a signal sent to the mobile unit. This signal command data is separated by the digital data receiver and interpreted by the control processor in setting the level. This signal as provided from the control processor is converted by a digital to analog (D/A) converter (not shown) before input to comparator 98.

The output of amplifier 104 is provided as an input to amplifier 102. Amplifier 102 as previously mentioned is also a variable gain IF amplifier with the gain determined according to the power level control signal output from filter 100. The signal for transmission is amplified in accordance with the gain set by the power level control signal from filter 100. The amplified output signal from amplifier 102 and is further amplified and frequency translated to the RF frequency for transmission. The RF signal is then fed to the antenna for transmission.

Figure 6:
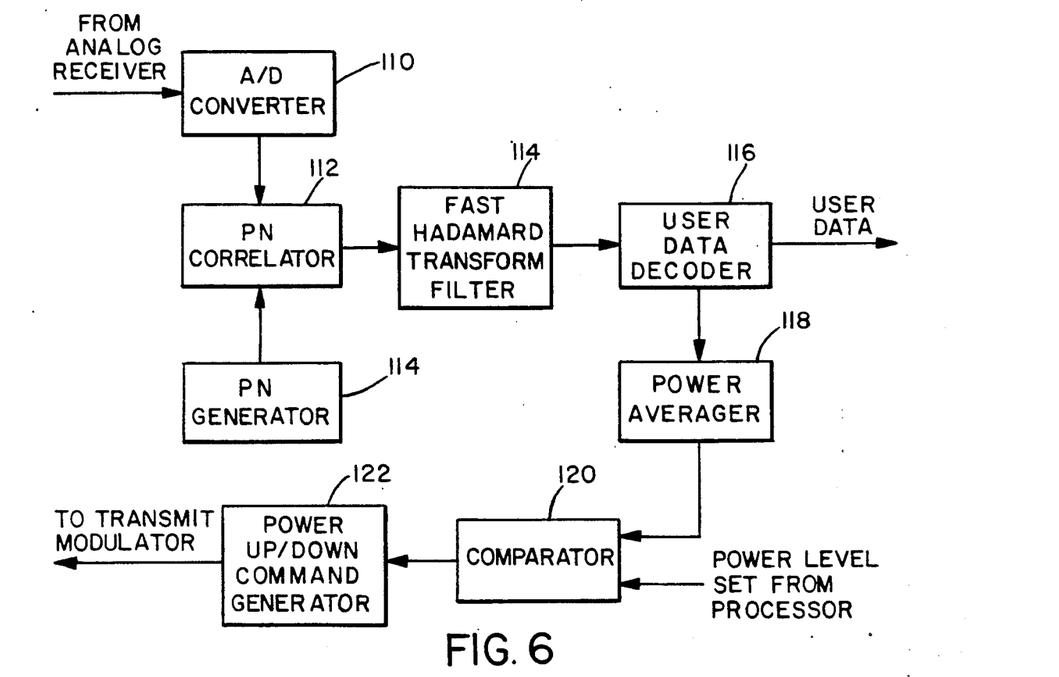
FIG. 6 is a block diagram illustrating in further detail the power control features of the cell-site of FIG. 3.

FIG. 6 illustrates in further detail the power control scheme of the cell-site as illustrated in FIG. 3. In FIG. 6 a mobile unit transmitted signal is received at the cell-site. The received signal is processed by the cell-site analog receiver and cell-site digital data receiver corresponding to mobile unit N.

In the digital data receiver, receiver 56 of FIG. 3, the received analog signal is converted from analog to digital form by A/D converter 110. The digital signal output from A/D converter is provided to pseudorandom noise (PN) correlator 112 where the signal undergoes a correlation process with a PN signal provided from PN generator 114. The output of PN correlator 112 is provided to a fast Hadamard transform digital filter 114 where the signal is filtered. The output of filter 114 is provided to a user data decoder circuit 116 which provides user data to the user digital baseband circuitry. Decoder 116 provides the largest transform filter symbols to power average circuit 118. The power averager circuit 118 averages the largest transform outputs over a one millisecond interval using well known digital techniques.

A signal indicative of each average power level is output from power averager 118 to comparator 120. Comparator 120 also receives a power level set signal indicative of the desired received power level. This desired received power level is set by the control processor for the cell-site. Comparator 120 compares the two input signals and provides an output signal indicative of the deviation of the average power level from the desired power level. This signal is provided output to power up/down command generator 122. Generator 122 in response to the comparison generates either a power-up or a power-down command. Power command generator 122 provides the power control commands to the cell-site transmit modulator for transmission and control of the transmitter power of mobile unit N.

If the received power at the cell-site is higher than that desired of mobile unit N, then a power-down command is generated and transmitted to mobile unit N. However, if the received power level at the cell-site is too low, then a power-up command is generated and transmitted. The up/down commands are transmitted at a high rate, nominally 1,000 commands per second in the exemplary embodiment. At one bit per command, the overhead of the power command is insignificant compared to the bit rate of a high quality digital voice signal.

The power adjustment command feedback compensates for changes in the inbound channel that are independent of the outbound channel. These independent inbound channel changes are not measured in the outbound channel signal. Therefore, the path loss estimate based upon the outbound channel and the corresponding transmitter power adjustment do not reflect the changes in the inbound channel. Thus, the power adjustment command feedback is used to compensate for adjustments in mobile unit transmitter power based on the inbound channel path losses that do not exist in the inbound channel.

In using a closed loop control process it is highly desirable for the command to arrive at the mobile unit before conditions change significantly. The present invention provides a novel and unique power control circuitry at the cell-site for minimizing delay and latency of measurement and transmission. The power control circuitry at the mobile unit, analog control and digital command response, provides a vastly improved power control process in the cellular mobile telephone system.

The previous description of the preferred embodiments are provided to enable any person skilled in the art to make or use the present invention. Various modifications to these embodiments will be readily apparent to those skilled in the art, and the generic principals defined herein may be applied to other embodiments without the use of the inventive faculty. Thus, the present invention is not intended to be limited to the embodiments shown herein, but is to be accorded the widest scope consistent with the principals and novel features disclosed herein.

We claim:

1. In a cellular mobile telephone system in which system users communicate information signals between one another via at least one cell-site using code division multiple access (CDMA) spread spectrum communication signals, a power control system for controlling transmission signal power for each mobile telephone in said cellular mobile telephone system, wherein each mobile telephone has an antenna, transmitter and receiver, and each cell-site has an antenna, at least one transmitter and at least one receiver, said power control system comprising:

at least one first power measurement means, each coupled to a respective mobile telephone receiver, for measuring signal power in CDMA communication signals received by said respective mobile telephone receiver;

at least one first power adjustment means, each coupled to a respective mobile telephone receiver and corresponding first power measurement means, said first power adjustment means responsive to decreases and increases in power measurements of said corresponding first power measurement means with respect to a first predetermined power level, for respectively increasing and decreasing transmission signal power of said corresponding mobile telephone transmitter;

at least one second power measurement means, each coupled to a respective cell-site receiver, for measuring signal power in each CDMA communication signal directed to said respective cell-site receiver from a corresponding mobile telephone transmitter in communication therewith;

at least one power adjustment command generator means, each coupled to a respective cell-site transmitter and corresponding second power measurement means, for generating power adjustment commands corresponding to deviations in power measurements of said corresponding second power measurement means from a second predetermined power level, said respective cell-site transmitter transmitting said power adjustment commands; and at least one second power adjustment means, each coupled to a respective mobile telephone receiver and corresponding transmitter, said second power adjustment means responsive to said power adjustment commands directed to said respective mobile telephone receiver, for adjusting transmission signal power of said corresponding mobile telephone transmitter.

2. The power control system of claim 1 wherein said first power adjustment means provided increase in transmission signal power is at a rate less than said first power adjustment means provided decrease in transmission signal power.

3. The power control system of claim 1 wherein said first power measurement means power measurements correspond to a sum of all contemporaneously received CDMA communication signals within a predetermined frequency band, and said first power measurement means is further for generating and providing a corresponding first power measurement signal to said corresponding first power adjustment means.

4. The power control system of claim 3 wherein said first power adjustment means comprises:

comparator means for receiving said first power measurement signal and a first power level set signal, said first power level set signal corresponding to a desired mobile telephone transmitter power level, for comparing said first power measurement signal with said first power level set signal, and for providing a corresponding comparator output signal; and variable gain amplification means operatively coupled to said mobile telephone transmitter for receiving said comparator output signal and responsive thereto for varying transmission signal power of said corresponding mobile telephone transmitter.

5. The power control system of claim 4 further comprising filter means disposed between said comparator means and said variable gain amplification means for receiving said comparator output signal, for unequally limiting a rate of change in increases and decreases in said received comparator output signal and for providing a corresponding limited comparator output signal to said variable gain amplification means.

6. An apparatus for controlling transmission signal power in a cellular mobile telephone in communications with at least one cell-site station using code division multiple access (CDMA) spread spectrum communication signals, said cellular mobile telephone having an antenna coupled to a transmitter and a receiver, said transmitter for generating and transmitting a CDMA carrier signal according to an assigned spreading function modulated by a mobile user input information signal, said receiver for receiving CDMA communication signals and spectrum processing said received CDMA communication signals according to an assigned spreading function so as to recover a mobile user output information signal intended for a user of said cellular mobile telephone, said cell-site station communicating power control commands in CDMA communication signals intended for said cellular mobile telephone with said receiver providing an output of said power control commands, said apparatus comprising:

measurement means for, operatively coupled to said receiver, measuring combined signal power in contemporaneously received CDMA communication signals and providing a measurement signal indicative of measured signal power;

adjustment means for, operatively coupling to said transmitter, receiving said measurement signal, varying transmitter signal power in opposite correspondence to variations in measured signal power about a predetermined power level; and additional adjustment means for, operatively coupled to said receiver and transmitter, receiving said power adjustment commands, and varying transmitter signal power in correspondence thereto.

7. The apparatus of claim 6 wherein said adjustment means is responsive to said measurement signal for, increasing transmitter signal power in response to decreases in measured signal power with respect to said predetermined power level, and decreasing transmitter signal power in response to increases in measured signal power with respect to said predetermined power level.

8. The apparatus of claim 7 wherein said adjustment means provided increase in transmitter signal power is at a rate less than said adjustment means provided decrease in transmitter signal power.

9. The apparatus of claim 6 wherein said cell-site station measures signal power of said cellular mobile telephone transmitted CDMA communication signals and generates for transmission said power adjustment commands indicative of one of an increase and a decrease in said cellular mobile telephone signal power so as to maintain a predetermined power level for cell-site station received CDMA communication signals from said cellular mobile telephone.

10. The apparatus of claim 6 wherein said adjustment means comprises:
   comparator means for receiving measurement signal and a first power level set signal, said first power level set signal corresponding to a desired cellular mobile telephone transmitter power level, for comparing said first power measurement signal with said first power level set signal, and for providing a corresponding comparator output signal;
   filter means for, receiving said comparator output signal, limiting a rate of change in variations in said comparator output signal, and providing an output of a corresponding limited comparator output signal; and
   variable gain amplification means, operatively coupled to said transmitter, for receiving said limited comparator output signal and responsive thereto for varying signal power of said transmitter.

11. The apparatus of claim 10 wherein said additional adjustment means comprises:
   processor means for, receiving said power adjustment commands, accumulating said power adjustment commands with a predetermined gain control level setting, and providing a corresponding power adjustment signal; and
   additional variable gain amplification means, operatively coupled to said transmitter, for receiving said power adjustment signal and responsive thereto for varying signal power of said transmitter.

12. In a cellular mobile telephone system in which system users communicate information signals between one another via at least one cell-site using code division multiple access (CDMA) spread spectrum communication signals, a method for controlling transmission signal power for each mobile telephone in said cellular mobile telephone system, wherein each mobile telephone has an antenna, transmitter and receiver, and each cell-site has an antenna, at least one transmitter and at least one receiver, said method comprising the steps of:
   measuring signal power in CDMA communication signals received by each respective mobile telephone receiver;
   varying transmission signal power of each corresponding mobile telephone transmitter in inverse proportion to variations in corresponding mobile telephone power measurements with respect to a first predetermined power level;
   measuring signal power in each CDMA communication signal received at each respective cell-site receiver as transmitted from a corresponding mobile telephone transmitter in communication therewith;
   generating power adjustment commands corresponding to deviations in corresponding cell-site power measurements from a second predetermined power level;
   transmitting said power adjustment commands along with said information signals rom each respective cell-site to a corresponding mobile telephone in communication therewith;
   receiving at each respective mobile telephone receiver said power adjustment commands corresponding thereto; and
   adjusting transmission signal power of each corresponding mobile telephone transmitter in correspondence to said power adjustment commands directed to said respective mobile telephone receiver.

13. The method of claim 12 wherein said step of varying transmission signal power of each corresponding mobile telephone transmitter in inverse proportion to variations in corresponding mobile telephone power measurements with respect to a first predetermined power level further comprises the step of:
   limiting a rate of increase in transmission signal power of each corresponding mobile telephone transmitter less than a rate of decrease in transmission signal power of each corresponding mobile telephone transmitter.

14. The method of claim 12 wherein said step of varying transmission signal power of each corresponding mobile telephone transmitter in inverse proportion to variations in corresponding mobile telephone power measurements with respect to a first predetermined power level comprises the steps of:
   providing an increase in transmission signal power of each corresponding mobile telephone transmitter in responsive to decrease in a corresponding mobile telephone power measurement with respect to said first predetermined power level; and
   providing an decrease in transmission signal power of each corresponding mobile telephone transmitter in response to an increase in a corresponding mobile telephone power measurement with respect to said first predetermined power level.

15. The method of claim 14 wherein said step of generating power adjustment commands corresponding to deviations in corresponding cell-site power measurements from a second predetermined power level comprises the steps of:
   generating a power-up command in response to a decrease in a corresponding cell-site power measurement from said second predetermined power level; and
   generating a power-down command in response to an increase in a corresponding cell-site power measurement from said second predetermined power level.

16. The method of claim 15 wherein said step of adjusting transmission signal power of each corresponding mobile telephone transmitter in correspondence to said power commands directed to said respective mobile telephone receiver comprises the steps of:
  increasing mobile telephone transmitter signal in response to each power-up command; and
  decreasing mobile telephone transmitter signal in response to each power-down command.

17. The method of claim 12 wherein said step of generating power adjustment commands corresponding to deviations in corresponding cell-site power measurements from a second predetermined power level comprises the steps of:
  generating a power-up command in response to a decrease in a corresponding cell-site power measurement from said second predetermined power level; and
  generating a power-down command in response to an increase in a corresponding cell-site power measurement from said second predetermined power level.

18. The method of claim 17 wherein said step of adjusting transmission signal power of each corresponding mobile telephone transmitter in correspondence to said power adjustment commands directed to said respective mobile telephone receiver comprises the steps of:
  increasing mobile telephone transmitter signal in response to each power-down command; and
  decreasing mobile telephone transmitter signal in response to each power-down command.

19. The method of claim 12 wherein in said step of measuring signal power in CDMA communication signals received by each respective mobile telephone receiver, measured signal power corresponds to a sum of all contemporaneously received CDMA communication signals within a predetermined frequency band.

20. The method of claim 12 further comprising the step of generating a first power measurement signal corresponding to said measured signal power in CDMA communication signals received by each respective mobile telephone receiver.

21. The method of claim 20 wherein said step of varying transmission signal power of each corresponding mobile telephone transmitter in inverse proportion to variations in corresponding mobile telephone power measurements with respect to a first predetermined power level comprises the steps of:
  comparing said first power measurement signal with a first power level set signal, said first power level set signal corresponding to a desired mobile telephone transmitter power level;
  providing a comparator output signal corresponding to a difference between said first power measurement signal and said first power level set signal; and
  varying mobile telephone transmitter gain according to said comparator output signal.

22. A method for controlling transmission signal power in a cellular mobile telephone in communications with at least one cell-site station using code division multiple access (CDMA) spread spectrum communication signals, said cellular mobile telephone having an antenna coupled to a transmitter and a receiver, said transmitter for generating and transmitting a CDMA carrier signal according to an assigned spreading function modulated by a mobile user input information signal, said receiver for receiving CDMA communication signals and spectrum processing said received CDMA communication signals according to an assigned spreading function so as to recover a mobile user output information signal intended for a user of said cellular mobile telephone, said cell-site station communicating power control commands in CDMA communication signals intended for said cellular mobile telephone with said receiver processing said received power control commands and providing an output of said power control commands, said method comprising the steps of:
  measuring combined signal power in contemporaneously received CDMA communication signals;
  varying transmitter signal power in inverse proportion to variations in measured signal power about a predetermined power level; and
  varying transmitter signal power in correspondence to received power adjustment commands.

23. The method of claim 22 wherein said step of varying transmitter signal power in inverse proportion to variations in measured signal power about a predetermined power level comprises the steps of:
  increasing transmitter signal power in response to decreases in measured signal power with respect to said predetermined power level; and
  decreasing transmitter signal power in response to increases in measured signal power with respect to said predetermined power level.

24. The method of claim 23 wherein increases in transmitter signal power are at a rate less than decreases in transmitter signal power.

25. The method of claim 22 wherein said cell-site station measures signal power of said cellular mobile telephone transmitted CDMA communication signals and generates for transmission said power adjustment commands indicative of one of an increase and a decrease in said cellular mobile telephone signal power so as to maintain a predetermined power level for cell-site station received CDMA communication signals from said cellular mobile telephone.

26. The method of claim 22 wherein said step of measuring combined signal power in contemporaneously received CDMA communication signals further comprises the step of generating a measurement signal indicative of measured signal power, and wherein said step of varying transmitter signal power in inverse proportion to variations in measured signal power about a predetermined power level comprises the steps of:
  generating a first power level set signal corresponding to a desired cellular mobile telephone transmitter power level;
  comparing said first power measurement signal with said first power level set signal;
  providing a comparator output signal corresponding to a difference between said desired cellular mobile telephone transmitter power level and said measured signal power;
  limiting a rate of change in variations in said comparator output signal;
  providing a corresponding limited comparator output signal; and
  varying signal power of said transmitter in response to said limited comparator output signal.

27. The method of claim 26 wherein said step of varying transmitter signal power in correspondence to received power adjustment commands comprises the steps of:
  accumulating said processed power adjustment commands with a predetermined gain control level setting;
  providing a power adjustment signal corresponding to said accumulation of said processed power adjustment commands with said predetermined gain control level setting; and
  varying signal power of said transmitter in response to said power adjustment signal.

* * * * *